US010624903B2

(12) United States Patent
Ahmed et al.

(10) Patent No.: US 10,624,903 B2
(45) Date of Patent: Apr. 21, 2020

(54) LONGER-ACTING PROGESTIN PRODRUG CONTRACEPTIVES

(71) Applicant: Evestra, Inc., Schertz, TX (US)

(72) Inventors: Gulzar Ahmed, San Antonio, TX (US); Frederick Meece, San Antonio, TX (US); Hareesh Nair, San Antonio, TX (US); Klaus Nickisch, Berlin (DE)

(73) Assignee: Evestra, Inc., Schertz, TX (US)

( * ) Notice: Subject to any disclaimer, the term of this patent is extended or adjusted under 35 U.S.C. 154(b) by 0 days.

(21) Appl. No.: 16/131,640

(22) Filed: Sep. 14, 2018

(65) Prior Publication Data

US 2019/0117670 A1 Apr. 25, 2019

Related U.S. Application Data

(60) Provisional application No. 62/574,445, filed on Oct. 19, 2017.

(51) Int. Cl.
*A61K 31/567* (2006.01)
*A61K 9/00* (2006.01)
*A61P 15/18* (2006.01)
*A61K 31/58* (2006.01)
*A61K 9/10* (2006.01)

(52) U.S. Cl.
CPC .......... *A61K 31/567* (2013.01); *A61K 9/0019* (2013.01); *A61K 9/10* (2013.01); *A61K 31/58* (2013.01); *A61P 15/18* (2018.01)

(58) Field of Classification Search
CPC .... A61K 31/567; A61K 9/0019; A61K 31/58; A61P 15/18
USPC .................................................. 514/255.05
See application file for complete search history.

(56) References Cited

U.S. PATENT DOCUMENTS

| | | | | |
|---|---|---|---|---|
| 3,051,731 | A | * | 8/1962 | Hull .......................... C07J 1/00 552/527 |
| 3,461,118 | A | | 8/1969 | Edwards |
| 3,514,514 | A | * | 5/1970 | Lehmann ............. A61K 31/569 514/178 |
| 4,507,290 | A | * | 3/1985 | Archer .................... C07C 51/36 514/172 |
| 4,615,835 | A | | 10/1986 | Eisenbrand et al. |
| 5,705,495 | A | | 1/1998 | Schwarz et al. |
| 6,080,735 | A | | 6/2000 | Schwarz et al. |
| 6,841,548 | B2 | | 1/2005 | Schwarz et al. |
| 6,956,031 | B2 | | 10/2005 | Hillisch et al. |
| 6,958,327 | B1 | | 10/2005 | Hillisch et al. |
| 7,507,725 | B2 | | 3/2009 | Elger et al. |
| 7,534,780 | B2 | | 5/2009 | Wyrwa et al. |
| 2004/0087565 | A1 | | 5/2004 | Kosemund et al. |
| 2005/0222114 | A1 | * | 10/2005 | De Nijs ................ A61K 31/568 514/182 |
| 2005/0277625 | A1 | * | 12/2005 | Wyrwa ...................... C07J 1/00 514/182 |
| 2005/0288267 | A1 | | 12/2005 | Wyrwa et al. |
| 2007/0037780 | A1 | | 2/2007 | Ebert et al. |
| 2007/0135375 | A1 | | 6/2007 | Wyrwa et al. |
| 2007/0135399 | A1 | * | 6/2007 | Wyrwa ..................... C07J 43/00 514/176 |
| 2007/0197488 | A1 | * | 8/2007 | Peters .................. C07J 41/0044 514/171 |
| 2007/0219169 | A1 | | 9/2007 | Becourt et al. |
| 2009/0186869 | A1 | | 7/2009 | Cottell et al. |
| 2010/0092463 | A1 | | 4/2010 | Ishikawa et al. |
| 2011/0250542 | A1 | | 10/2011 | Liu et al. |
| 2012/0065179 | A1 | * | 3/2012 | Andersson ............. A61K 31/19 514/179 |
| 2015/0018322 | A1 | * | 1/2015 | Nickisch ................ C07J 43/003 514/176 |

FOREIGN PATENT DOCUMENTS

| | | |
|---|---|---|
| CA | 2091268 | 3/1992 |
| CN | 102079771 | 6/2011 |
| CN | 102127137 | 7/2011 |
| EP | 0129947 | 1/1985 |
| EP | 0351561 | 1/1990 |
| FR | 2774989 | 8/1999 |
| GB | 753793 | * 8/1956 |

OTHER PUBLICATIONS

Gould; J. Am. Chem. Soc., 1957, 79 , 4472-4475. (Year: 1957).*
Karunanithy; J.Pharmacobio-Dyn. 1989, 12, 468-475. (Year: 1989).*
Meece; Steroids 137 (2018) 47-56. (Year: 2018).*
Schonecker; Angew. Chem. Int. Ed. 2003, 42, 3240-3244. (Year: 2003).*
International Search Report for PCT Application No. PCT/US2014/046353 dated Oct. 15, 2014.
Written Opinion for PCT Application No. PCT/US2014/046353 dated Oct. 15, 2014.
Boyle et al. "A new synthesis of difluoromethanesulfonamides—a novel pharmacophore for carbonic anhydrase inhibition" Org. Biomol. Chem., 2005,3, 222-224.
Hassan et al. "Synthesis, antimicrobial and antiviral testing of some new 1-adamantyl analogues" Saudi Pharmaceutical Journal (2010) 18, 123-128.
PubChem CID 42937895, Jul. 20, 2009, pp. 1-3 [online].
PubChem CID 9166052 , Jul. 31, 2006, pp. 1-4 [online].
PubChem CID 799253 , Jul. 9, 2005, pp. 1-5 [online].
PubChem CID 8421747 , Jul. 30, 2006, pp. 1-3 [online].
PubChem CID 56865468 , Mar. 30, 2012, pp. 1-3 [online].
Elger et al. "Sulfamates of various estrogens are prodrugs with increased systemic and reduced hepatic estrogenicity at oral application" J. Steroid Biochem. Molec. Biol. 55, 3-4, Dec. 1995, pp. 395-403.
Li et al. "A Facile Synthesis of 1-Substituted Cyclopropyl sulfonamides" Synlett (2006) 5:725.
Iyer et al. "Inhibition Profiling of Human Carbonic Anhydrase II by High-Throughput Screening of Structurally Diverse, Biologically Active Compounds" Journal of Biomolecular Screening 2006:782-791.

(Continued)

*Primary Examiner* — Daniel R Carcanague
(74) *Attorney, Agent, or Firm* — Kowert, Hood, Munyon, Rankin & Goetzel, P.C.; Mark R. DeLuca

(57) ABSTRACT

Described herein are progestin compounds that have extended release rates and that can be used without an estrogen to produce a contraceptive state.

14 Claims, No Drawings

(56) References Cited

OTHER PUBLICATIONS

McNatty et al. "Concentration of Oestrogens and Androgens in Human Ovarian Venous Plasma and Follicular Fluid Throughout the Menstrual Cycle" J Endocrinol Oct. 1, 1976 71 17-85.
PubChem CID 68119304, pp. 1-13, Nov. 30, 2012, pp. 4.
PubChem CID 23623931 pp. 1-12, Dec. 12, 2007, pp. 4.
International Search Report and Written Opinion for PCT Application No. PCT/US2018/051026 dated Oct. 24, 2018.

* cited by examiner

LONGER-ACTING PROGESTIN PRODRUG CONTRACEPTIVES

PRIORITY CLAIM

This application claims priority to U.S. Provisional Application Ser. No. 62/574,445 entitled "LONGER-ACTING PROGESTIN PRODRUG CONTRACEPTIVES" filed Oct. 19, 2017, which is incorporated herein by reference in its entirety.

BACKGROUND OF THE INVENTION

1. Field of the Invention

The invention generally relates to contraceptives. More particularly, the invention relates to progestin compounds that have extended release rates and that can be used without an estrogen to produce a contraceptive state.

2. Description of the Relevant Art

The currently available steroid based fertility control methods rely either on a combination of an estrogen, in most cases ethinyl estradiol and a progestin or on progestin alone. The primary contraceptive mechanism is inhibition of gonatropin secretion thereby inhibiting follicular development and ovulation.

Recently, there is an increased interest in progestin only contraceptive products and products that offer longer contraceptive effects. This is based on the finding that progestin only products have lower rates of deep vein thrombosis compared to the classical ethinyl estradiol containing products. The interest in longer acting contraceptive products is in part driven by the desire to provide safe and effective contraceptive methods to women in the sub-Sahara area that cannot get access to modern contraceptive products. The only currently available 3 month injectable product, Depo Provera, uses medroxyprogesterone acetate (MPA) as progestin. MPA has some undesirable effects, such as an increase of insulin levels, reduction of bone mass density, weight gain and enhanced risks for HIV infections.

There is a clear need for a safe and effective progestin only product that could provide contraceptive effect for up to 6 months with just one subcutaneous injection.

This need was already acknowledged in 1975 by the WHO Chemical Synthesis Programme with the goal to develop 3-6 month progestin-only injections.

Extensive work has been performed in this area and more than 200 derivatives of norethisterone and levonorgestrel were synthesized and characterized (see Bially et al. in Steroids 41, 419 1983). Most of these derivatives were esters of the parent progestins in the 17 position (U.S. Pat. No. 4,507,290, EP 129947). Levonorgestrel butanoate was selected for development, but failed in the clinic to reach a contraceptive effect for up to 6 month. Other esters of levonorgestrel and etonogestrel have been described. Undecanoate esters of etonogestrel have been used for the treatment of gynecological disorders, however these esters only exhibited a contraceptive effect for around 4 weeks.

U.S. Pat. No. 4,794,119 describes "Aqueous Crystalline Suspension of Glycoesters" of progestins like levonorgestrel and etonogestrel. Upon a one-time intramuscular injection of 30-75 mg of steroid glycoester as an aqueous crystalline suspension, a steroid level is achieved in the plasma which over a period of 4 weeks, is adequately high and shows a uniform course.

In summary it can be stated that although esters of levonorgestrel and etonogestrel have been prepared, none of these derivatives has exhibited a long-lasting antiovulatory effect after subcutaneous application.

SUMMARY OF THE INVENTION

The current invention describes an unexpected solution to the above problem. Simple esters of progestins, such as levonorgestrel and etonogestrel, with phenoxy-acetic acid exhibited a significantly longer antiovulatory effect in test animals than MPA or levonorgestrel butanoate. This result is unexpected when taking into account that more than 200 esters of levonorgestrel with numerous aliphatic, saturated and unsaturated acids have been described in the WHO program without reaching the goal of a 6 month contraceptive effect in women.

It is especially noteworthy and unexpected that in the described case, the simplest unsubstituted phenoxy-acetic acid esters provide the longest anti-ovulatory effect in test animals, considering the long-standing past studies of esters of levonorgestrel.

In an embodiment, a compound has the structural formula I:

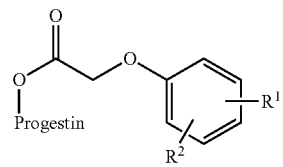

III where,
progestin is levonorgestrel or etonogestrel;
$R_1$, $R_2$ combine together to form a fused 3 to 7 membered ring with up to two heteroatoms, or each $R_1$, $R_2$, is, independently H, alkyl, cycloalkyl, phenyl, aryl, heteroaryl, acyl, cyano, halogen, OH, alkoxy, alkyl-sulfonyl or sulfonamide.

In an embodiment, a compound has structural formula II:

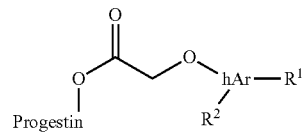

IV where,
progestin is levonorgestrel or etonogestrel;
hAr is pyridine, pyrimidine, pyrazine or oxazole;
$R_1$, $R_2$ combine together to form a fused 3 to 7 membered ring with up to two heteroatoms, or each $R_1$, $R_2$, is, independently H, alkyl, cycloalkyl, phenyl, aryl, heteroaryl, acyl, cyano, halogen, OH, alkoxy, alkyl-sulfonyl or sulfonamide.

In an embodiment, a method of producing a contraceptive state in a subject comprising administering an effective amount of a compound, as described herein, to the subject. The compound may be administered by subcutaneous injection. Preferably, the compound has a biological effect lasts for at least 6 months.

In an embodiment, the 17-hydroxy function of levonorgestrel or etononorgestrel derivatives are esterified to form esters of phenoxy acetic acid.

DETAILED DESCRIPTION OF THE PREFERRED EMBODIMENTS

It is to be understood the present invention is not limited to particular devices or methods, which may, of course, vary. It is also to be understood that the terminology used herein is for the purpose of describing particular embodiments only, and is not intended to be limiting. As used in this specification and the appended claims, the singular forms "a", "an", and "the" include singular and plural referents unless the content clearly dictates otherwise. Furthermore, the word "may" is used throughout this application in a permissive sense (i.e., having the potential to, being able to), not in a mandatory sense (i.e., must). The term "include," and derivations thereof, mean "including, but not limited to." The term "coupled" means directly or indirectly connected.

The term "alkyl" as used herein generally refers to a radical substituent containing the monovalent group $C_nH_{2n}$, where n is an integer greater than zero. In some embodiments n is 1 to 12, in other embodiments n is 1 to 6. The term "alkyl" includes a branched or unbranched monovalent hydrocarbon radical. Examples of alkyl radicals include, but are not limited to: methyl, ethyl, propyl, isopropyl, butyl, iso-butyl, sec-butyl, pentyl, 3-pentyl, hexyl, heptyl, octyl, nonyl, decyl, undecyl, dodecyl. When the alkyl group has from 1-6 carbon atoms, it is referred to as a "lower alkyl." Suitable lower alkyl radicals include, but are not limited to, methyl, ethyl, n-propyl, i-propyl, 2-propenyl (or allyl), n-butyl, t-butyl, and i-butyl (or 2-methylpropyl).

The term "cycloalkyl" as used herein generally refers to a radical substituent containing the monovalent group $C_nH_{2n-1}$, where n is an integer greater than zero and wherein the carbons $C_1$ and $C_n$ are coupled to each other to form a ring. In some embodiments n is 3 to 8. Examples of cycloalkyl radicals include, but are not limited to: cyclopropyl (n=3), cyclobutyl (n=4), cyclopentyl (n=5), cyclohexyl (n=6), cycloheptyl (n=7), and cyclooctyl (n=8).

The term "alkoxy" generally refers to an —OR group, where R is a lower alkyl, substituted lower alkyl, aryl, substituted aryl, aralkyl or substituted aralkyl. Suitable alkoxy radicals include, but are not limited to, methoxy, ethoxy, phenoxy, t-butoxy, methoxyethoxy, and methoxymethoxy.

The term alkyl-sulfonyl refers to the group —SO$_2$-alkyl, where alkyl is as defined above. Preferably alkyl is $C_1$-$C_6$ alkyl.

The term sulfonamide refers to the group —SO$_2$—NR'R", where R' and R" are each, independently, alkyl or phenyl. Preferably, R' and R" are $C_1$-$C_6$ alkyl.

Aromatic heterocyclic compounds are also referred to as "heteroaryls." Heteroaryls may include rings such as thiophene, pyridine, isoxazole, phthalimide, pyrazole, indole, furan, pyrimidine, pyrazine or oxazole or benzo-fused analogs of these rings. In some embodiments, a "heteroaryl" is a stable 5- to 7-membered monocyclic or bicyclic or 7- to 10-membered bicyclic heterocyclic ring which is either saturated or unsaturated, and which consists of carbon atoms and from 1 to 4 heteroatoms (e.g., N, O, and S) and wherein the nitrogen and sulfur heteroatoms may optionally be oxidized, and the nitrogen may optionally be quaternized, and including any bicyclic group in which any of the above-defined heterocyclic rings is fused to a benzene ring. In some embodiments, heterocycles may include cyclic rings including boron atoms. The heterocyclic ring may be attached to its pendant group at any heteroatom or carbon atom that results in a stable structure. The heterocyclic rings described herein may be substituted on carbon or on a nitrogen atom if the resulting compound is stable. Examples of such heterocycles include, but are not limited to, 1H-indazole, 2-pyrrolidonyl, 2H,6H-1,5,2-dithiazinyl, 2H-pyrrolyl, 3H-indolyl, 4-piperidonyl, 4aH-carbazole, 4H-quinolizinyl, 6H-1,2,5-thiadiazinyl, acridinyl, azocinyl, benzofuranyl, benzothiophenyl, carbazole, chromanyl, chromenyl, cinnolinyl, decahydroquinolinyl, furanyl, furazanyl, imidazolidinyl, imidazolinyl, imidazolyl, indolinyl, indolizinyl, indolyl, isobenzofuranyl, isochromanyl, isoindolinyl, isoindolyl, isoquinolinyl (benzimidazolyl), isothiazolyl, isoxazolyl, morpholinyl, naphthyridinyl, octahydroisoquinolinyl, oxazolidinyl, oxazolyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridinyl, pyridyl, pyrimidinyl, pyrrolidinyl, pyrrolinyl, pyrrolyl, quinazolinyl, quinolinyl, quinoxalinyl, quinuclidinyl, carbolinyl, tetrahydrofuranyl, tetrahydroisoquinolinyl, tetrahydroquinolinyl, tetrazolyl, thianthrenyl, thiazolyl, thienyl, thiophenyl, triazinyl, xanthenyl. Also included are fused ring and spiro compounds containing, for example, the above heterocycles.

In the first embodiment ester derivatives are being described that have the following general formula I:

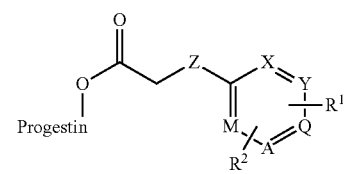

Where:
progestin is levonorgestrel or etonogestrel;
Z is C, NH, N-alkyl, O, or S;
A, M, Q X, and Y are each, independently, C or N;
$R_1$, $R_2$ can combine together to form a fused cycloalkyl ring or a fused 3 to 7 membered ring with up to two heteroatoms, or each $R_1$, $R_2$, can independently, be H, alkyl, cycloalkyl, phenyl, aryl, heteroaryl, acyl, cyano, halogen, OH, alkoxy, alkyl-sulfonyl or sulfonamide.

In another embodiment ester derivatives are being described that have the following general formula II:

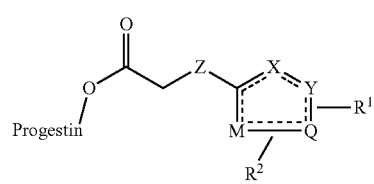

Where:
progestin is levonorgestrel or etonogestrel;
Z is C, NH, N-alkyl, O, or S;
M, Q, X, Y are each, independently, C, N, O or S;

$R_1$, $R_2$ can combine together to form a fused cycloalkyl ring or a fused 3 to 7 membered ring with up to two heteroatoms, or each $R_1$, $R_2$, can independently, be H, alkyl, cycloalkyl, phenyl, aryl, heteroaryl, acyl, cyano, halogen, OH, alkoxy, alkyl-sulfonyl or sulfonamide.

In a preferred embodiment, a compound has the structural formula I:

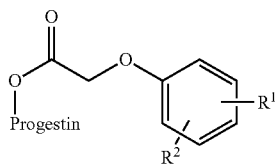

where,
progestin is levonorgestrel or etonogestrel; and
$R_1$, $R_2$ combine together to form a fused 3 to 7 membered ring with up to two heteroatoms, or each $R_1$, $R_2$, is, independently H, alkyl, cycloalkyl, phenyl, aryl, heteroaryl, acyl, cyano, halogen, OH, alkoxy, alkyl-sulfonyl or sulfonamide.

In another preferred embodiment, a compound has structural formula II:

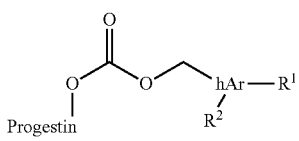

where,
progestin is levonorgestrel or etonogestrel;
hAr is pyridine, pyrimidine, pyrazine or oxazole; and
$R_1$, $R_2$ combine together to form a fused 3 to 7 membered ring with up to two heteroatoms, or each $R_1$, $R_2$, is, independently H, alkyl, cycloalkyl, phenyl, aryl, heteroaryl, acyl, cyano, halogen, OH, alkoxy, alkyl-sulfonyl or sulfonamide.

In an embodiment, a method of producing a contraceptive state in a subject comprises administering an effective amount of a compound, as described herein, to the subject. The compound may be administered by subcutaneous injection. Preferably, the compound has a biological effect lasts for at least 6 months.

In an embodiment, the 17-hydroxy function of levonorgestrel or etononorgestrel derivatives are esterified to form esters of phenoxy acetic acid.

EXPERIMENTAL

Synthesis

In one embodiment, the compounds described herein may be synthesized according to the general Scheme 1 below.

Scheme 1

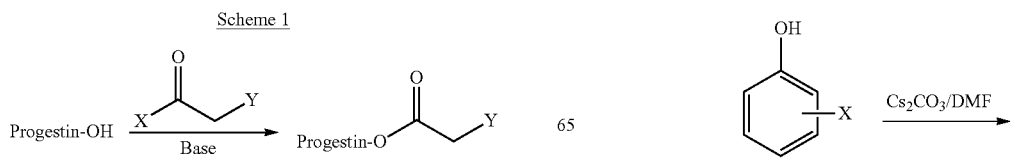

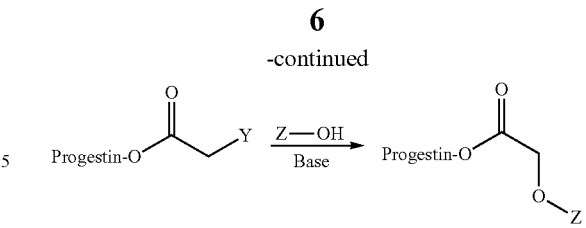

In Scheme 1, X is a labile group conducive to acylation. Y is also a labile group. In some embodiments, X is a halogen or O—C(O)—CH$_2$—Y to form an anhydride. Y is a group suitable for nucleophilic substitution such as a halide or alkoxy group. In a preferred embodiment, Y is a halogen (Cl or Br). The group Z represents the substituent (V) or (VI), where $R_1$ and $R_2$ are as defined above for compounds (I) and (II).

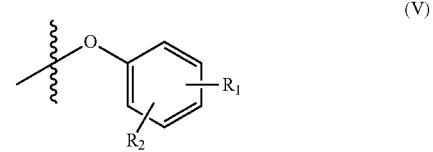

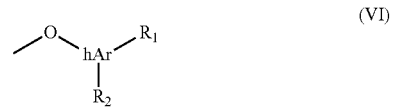

A specific example of a compound made using the procedure of Scheme 1 is shown below in Scheme 2.

Scheme 2

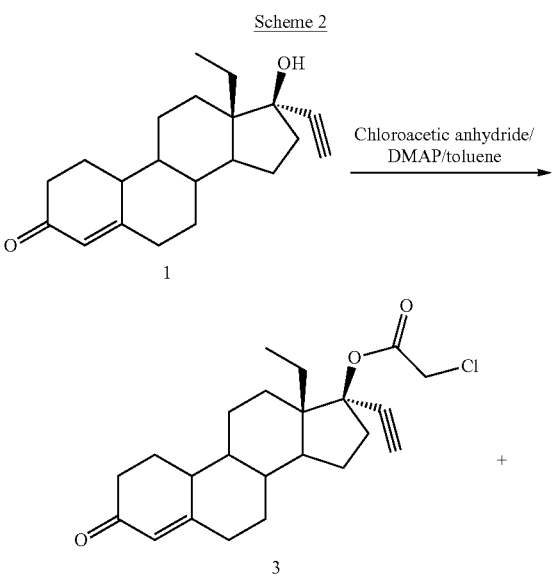

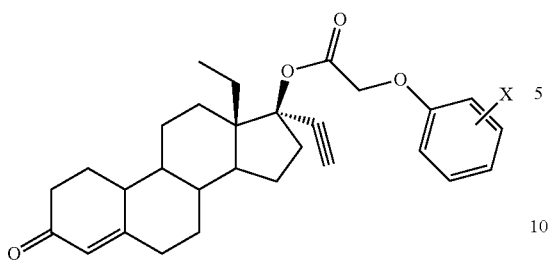

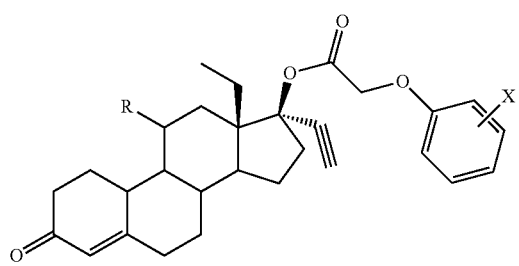

In one embodiment, the compounds described herein may be synthesized according to the general Scheme 3 below.

Scheme 3

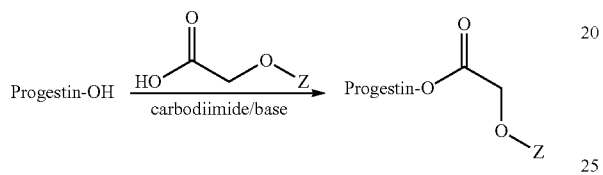

In Scheme 3, a Steglich esterification is used to form an ester between the progestin alcohol and the acetic acid portion of the prodrug component. The reaction uses a carbodiimide and a base. Suitable carbodimides include, but are not limited to, dicyclohexylcarbodiimide and diisopropylcarbodiimide. Any suitable base can be used. Preferably the base is a pyridine base such as dimethylaminopyridine (DMAP). The group Z represents the substituent (V) or (VI), where $R_1$ and $R_2$ are as defined above for compounds (I) and (II).

A specific example of a compound made using the procedure of Scheme 2 is shown below in Scheme 4.

Scheme 4

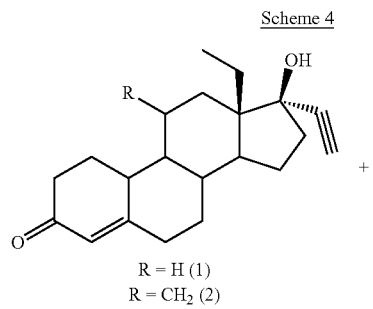

R = H (1)
R = CH$_2$ (2)

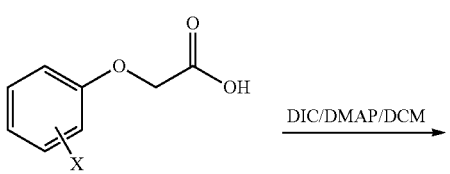
DIC/DMAP/DCM →

In some embodiments, when a Steglich esterification is used, a protecting groups may be used on the some of the pendant side chains. When the prodrug component includes a sulfonamide side chain a Scheme 5

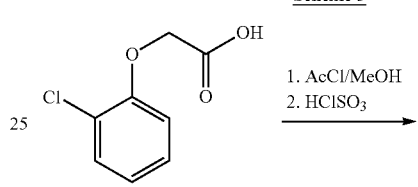

1. AcCl/MeOH
2. HClSO$_3$

1. TEA/DCM
2. LiOH—H$_2$O/THF 1. 1/DIC/DMAP/DCM
2. TFA/DCM

-continued

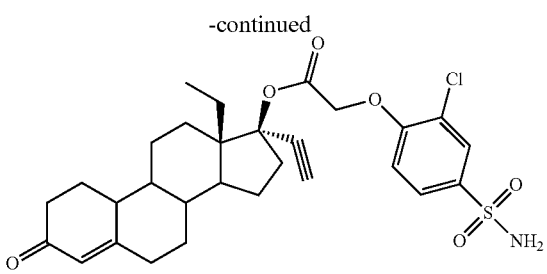

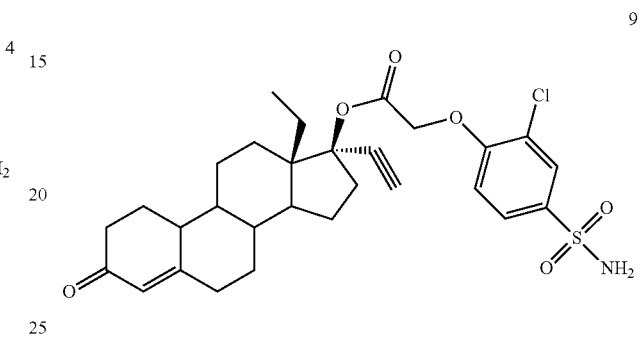

9

DMAP (550 mg, 4.5 mmol) in DCM (30 mL) at ambient temperature. Once a homogenous solution was observed, DIC was added (2.8 ml, 18.1 mmol). The mixture was allowed to stir overnight. The next morning the mixture was filtered, and the filtrate was rotovaped onto silica gel and subjected to flash chromatography. The resultant foam was then crystallized from methanol and DCM yielding 1.08 g of white crystal 5 (73%). 1H NMR (300 MHz, CDCl3) δ 7.17 (t, J=7.5 Hz, 1H), 6.81 (d, J=7.2 Hz, 1H), 6.73-6.67 (m, 2H), 5.84 (s, 1H), 4.59 (s, 2H), 2.66 (s, 1H), 2.33 (s, 3H).

4

(13S,17R)-13-ethyl-17-ethynyl-3-oxo-2,3,6,7,8,9,10, 11,12,13,14,15,16,17-tetradecahydro-1H-cyclopenta [a]phenanthren-17-yl (3-sulfamoylphenoxy)acetate (General Method #1)

To an oven-dried round bottom flask was added 3 (973 mg, 2.5 mmol), 3-hydroxybenzenesulfonamide (from PCT Int. Appl., 2004066963, 516 mg, 3.0 mmol), and 4A molecular sieve. Anhydrous DMF was added (5 ml) and then cesium carbonate (814 mg, 2.5 mmol). The mixture was allowed to stir for 24 hours, after which time an additional 0.5 equivalent of base and 0.3 equivalent of phenol was added to fully convert the starting material by allowing to stir an additional 16 hours. The mixture was then diluted with ice-cold saturated sodium bicarbonate and the resulting solids collected by vacuum filtration, washed with water and allowed to air-dry. The product was isolated by subjecting the crude solid to flash chromatography using a 2 to 10% gradient of acetone in DCM to afford 4. 1H NMR (300 MHz, DMSO-d6) δ 7.52-7.31 (m, 4H), 7.13 (ddd, J=7.8, 2.4, 0.9 Hz, 1H), 5.73 (s, 1H), 4.83 (s, 2H), 3.65 (s, 1H).

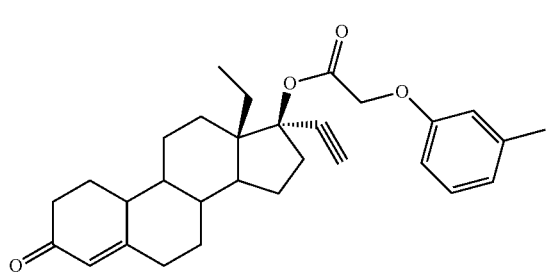

5

(13S,17R)-13-ethyl-17-ethynyl-3-oxo-2,3,6,7,8,9,10, 11,12,13,14,15,16,17-tetradecahydro-1H-cyclopenta [a]phenanthren-17-yl (3-methylphenoxy)acetate (General Method #2)

To a round bottom flask was added 1 (1.41 g, 4.5 mmol), (3-methylphenoxy)acetic acid (3.0 g, 18.1 mmol), and (13S,17R)-13-ethyl-17-ethynyl-3-oxo-2,3,6,7,8,9,10, 11,12,13,14,15,16,17-tetradecahydro-1H-cyclopenta [a]phenanthren-17-yl (2-chloro-4-sulfamoylphenoxy)acetate (General Method #3)

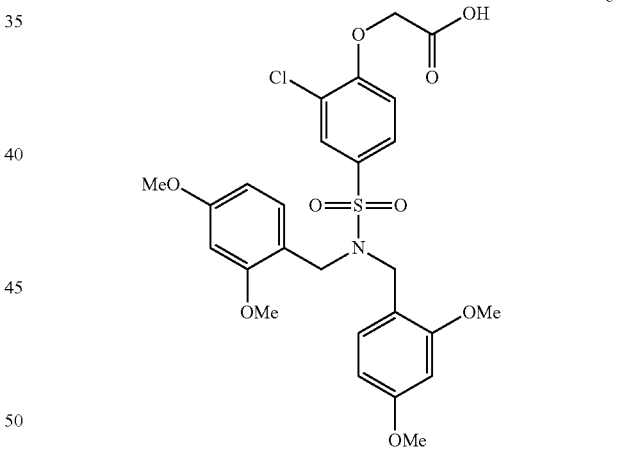

8

Formation of (4-{bis[(2,4-dimethoxyphenyl)methyl] sulfamoyl}-2-chlorophenoxy)acetic acid 8

2-Chlorophenoxyacetic acid (2.31 g, 12.4 mmol) was dissolved in methanol, and 3 ml of acetyl chloride was added dropwise. The mixture was allowed to stir overnight, then the methanol was removed under vacuum, and the residue dissolved in DCM and washed with saturated sodium bicarbonate. The material was then used in the next step, which involved treating with 8.0 ml (0.124 mol) of chlorosulfonic acid which was added dropwise to the neat ester at 0° C., and then allowed to stir overnight while gradually warming to room temperature. The homogenous mixture was then diluted with DCM and then poured onto ice. The resulting layers were separated, and the aqueous extracted with DCM. The combined organics were washed with brine, dried over sodium sulfate, the solution was filtered and then concentrated to give 3.2 g (86%) of purplish crystalline solid [2-chloro-4-(chlorosulfonyl)phenoxy]acetic acid, methyl ester 6. $^1$H NMR (300 MHz, CDCl$_3$) δ 8.10 (d, J=2.7 Hz, 1H), 7.91 (dd, J=9.0, 2.4 Hz, 1H), 6.95 (d, J=9.0 Hz, 1H), 4.87 (s, 2H), 3.86 (s, 3H). This material was then placed in a round bottom flask, suspended in DCM (20 ml) and chilled to 0° C. 3.37 g (10.7 mmol) of Bis(2,4-Dimethoxybenzyl) amine (prepared as described in Organic and Biomolecular Chemistry, 10(37), 7610-7617, 2012) and TEA (3.0 ml, 21.4 mmol) were dissolved in DCM (30 ml) and added dropwise to the halide solution. The mixture was then allowed to gradually warm to room temperature while stirring overnight. The next day the mixture was evaporated onto silica and subjected to flash chromatography using a 0 to 10% gradient of EtOAc in DCM to obtain 5.79 g (93%) of the intermediate methyl (4-{bis[(2,4-dimethoxyphenyl)methyl] sulfamoyl}-2-chlorophenoxy)acetate 7 as a semi-crystalline solid $^1$H NMR (300 MHz, CDCl$_3$) δ 7.54 (d, J=2.1 Hz, 1H), 7.47 (dd, J=8.7 Hz, 1H), 7.19 (d, J=8.4 Hz, 2H), 6.71 (d, J=8.7 Hz, 1H), 6.42 (dd, J=8.4, 2.4 Hz, 2H), 6.29 (d, J=2.1 Hz, 2H), 4.76 (s, 2H), 4.39 (s, 4H), 3.84 (s, 3H), 3.80 (s, 6H), 3.65 (s, 6H). The methyl ester was saponified by treating with 10 ml of 5M LiOH—H$_2$O in 100 ml THF to afford acid 8 (5.65 g, 99%).

A round bottom flask was charged with 1 (780 mg, 2.5 mmol), 8 (5.6 g, 10 mmol), and DMAP (305 mg, 2.5 mmol). The solids were dissolved in DCM (30 ml) and then DIC was added (1.5 ml, 10 mmol), and the mixture was allowed to stir overnight. Next day, HPLC analysis indicated about 85% conversion of starting material. The mixture was filtered, loaded onto silica gel and subjected to flash chromatography using 2-5% gradient of acetone in DCM, and then 40% acetone in hexanes. The material was then dissolved in DCM (10 ml) and chilled to 0° C. 5 ml (65 mmol) of TFA was added. The mixture was allowed to stir for one hour, then the volatiles removed under vacuum and the residue washed with saturated sodium bicarbonate and the resulting solids collected by vacuum filtration. After drying, the solids were subjected to flash chromatography using 10% acetone in DCM, to furnish 754 mg of product 9 (54%, 2 steps)—1H NMR (300 MHz, DMSO-d6) δ 7.85 (d, J=2.4 Hz, 1H), 7.71 (dd, J=8.7, 2.1 Hz, 1H), 7.38 (s, 2H), 7.19 (d, J=8.7 Hz, 1H), 5.73 (s, 1H), 5.02 (dd, J=16.8, 5.1 Hz, 2H), 3.68 (s, 1H).

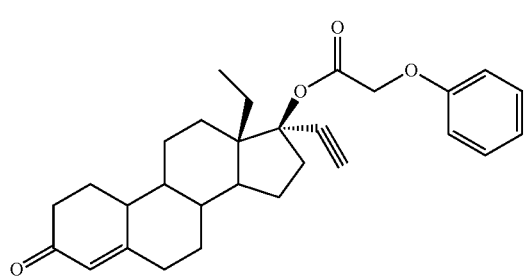

(13S,17R)-13-ethyl-17-ethynyl-3-oxo-2,3,6,7,8,9,10, 11,12,13,14,15,16,17-tetradecahydro-1H-cyclopenta [a]phenanthren-17-yl phenoxyacetate 10

Prepared in accordance with general method #2—$^1$H NMR (δ, CDCl3 300 MHz): 7.29 (dt, 2H, ArH, J=6.6, 0.9 Hz), 7.00 (dt, 1H, ArH, J=7.0, 0.9 Hz), 6.89 (d, 2H, ArH, J=8.1, 0.9 Hz), 5.84 (s, 1H), 4.61 (s, 2H), 2.82 (m, 2H), 2.65 (s, 1H) 0.99 (t, 3H, CH3, J=7.2 Hz).

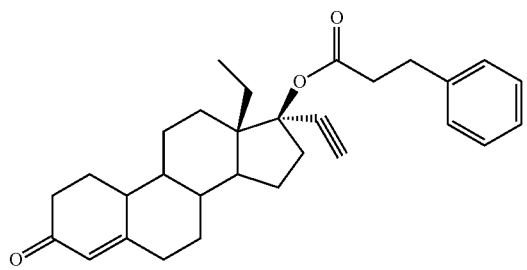

(13S,17R)-13-ethyl-17-ethynyl-3-oxo-2,3,6,7,8,9,10, 11,12,13,14,15,16,17-tetradecahydro-1H-cyclopenta [a]phenanthren-17-yl 3-phenylpropanoate 11

Prepared in accordance with general method #2—1H NMR (δ, CDCl3 300 MHz): 7.24 (m, 5H, ArH), 5.83 (s, 1H), 2.95 (t, 2H, J=7.9 Hz), 2.60 (s, 1H) 0.99 (t, 3H, CH3, J=7.3 Hz).

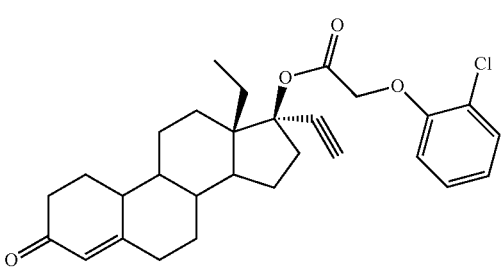

(13S,17R)-13-ethyl-17-ethynyl-3-oxo-2,3,6,7,8,9,10, 11,12,13,14,15,16,17-tetradecahydro-1H-cyclopenta [a]phenanthren-17-yl (2-chlorophenoxy)acetate 12

Prepared in accordance with general method #2—$^1$H NMR (300 MHz, CDCl3) δ 7.39 (dd, J=7.8, 1.5 Hz, 1H), 7.25-7.17 (m, 1H), 6.96 (td, J=7.8, 1.5 Hz, 1H), 6.84 (dd, J=8.4, 0.9 Hz, 1H), 5.84 (s, 1H), 4.70 (s, 2H), 2.66 (s, 1H).

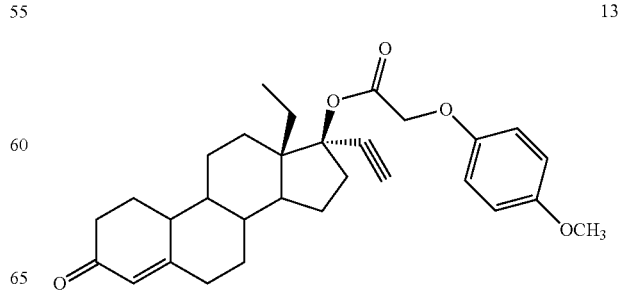

13

(13S,17R)-13-ethyl-17-ethynyl-3-oxo-2,3,6,7,8,9,10,
11,12,13,14,15,16,17-tetradecahydro-1H-cyclopenta
[a]phenanthren-17-yl (4-methoxyphenoxy)acetate
13

Prepared in accordance with general method #2—(300 MHz, CDCl3) δ 6.84 (s, 4H), 5.84 (s, 1H), 4.56 (s, 2H), 3.78 (s, 3H), 2.66 (s, 1H).

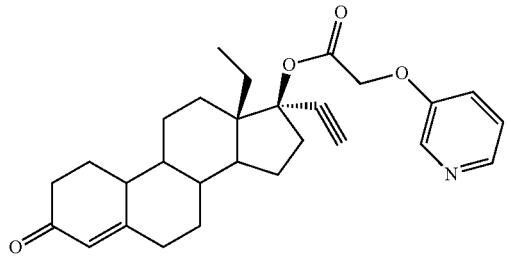

(13S,17R)-13-ethyl-17-ethynyl-3-oxo-2,3,6,7,8,9,10,
11,12,13,14,15,16,17-tetradecahydro-1H-cyclopenta
[a]phenanthren-17-yl [(pyridin-3-yl)oxy]acetate 14

Prepared in accordance with general method #2—$^1$H NMR (300 MHz, CDCl3) δ 8.33-8.27 (m, 2H), 7.30-7.18 (m, 2H), 5.85 (s, 1H), 4.66 (s, 2H), 2.68 (1H).

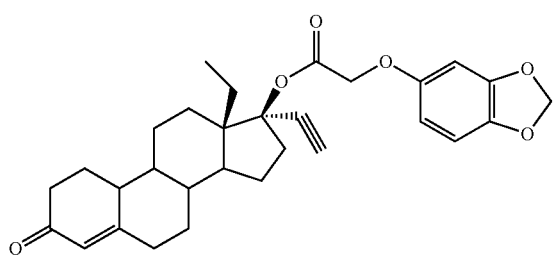

(13S,17R)-13-ethyl-17-ethynyl-3-oxo-2,3,6,7,8,9,10,
11,12,13,14,15,16,17-tetradecahydro-1H-cyclopenta
[a]phenanthren-17-yl [(2H-1,3-benzodioxol-5-yl)
oxy]acetate 15

Prepared in accordance with general method #1. 1H NMR (δ, CDCl3 300 MHz): 6.69 (d, 1H, ArH, J=7.8 Hz), 6.51 (d, 1H, ArH, J=2.7 Hz), 6.29 (dd, 1H, ArH, J=2.7, 8.7 Hz), 5.93 (s, 2H), 5.84 (s, 1H), 4.52 (s, 2H), 2.82 (m, 1H), 2.65 (s, 1H) 1.00 (t, 3H, CH3, J=7.0 Hz).

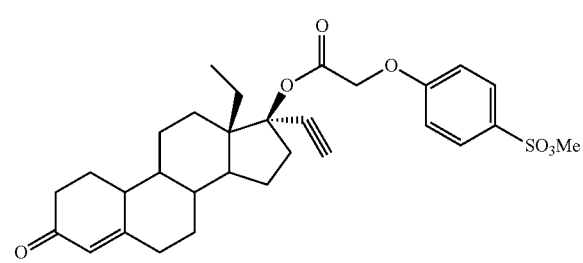

14

(13S,17R)-13-ethyl-17-ethynyl-3-oxo-2,3,6,7,8,9,10,
11,12,13,14,15,16,17-tetradecahydro-1H-cyclopenta
[a]phenanthren-17-yl [4-(methanesulfonyl)phenoxy]
acetate 16

Prepared in accordance with general method #1. 1H NMR (δ, CDCl3 300 MHz): 7.88 (dd, 2H, ArH, J=2.1, 6.9 Hz), 7.01 (dd, 2H, ArH, J=2.1, 6.9 Hz), 5.84 (s, 1H), 4.69 (s, 3H), 3.03 (s, 2H), 2.80 (m, 1H), 2.68 (s, 1H) 0.97 (m, 3H, CH3).

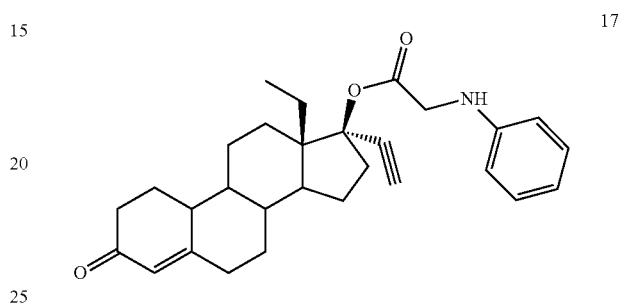

(13S,17R)-13-ethyl-17-ethynyl-3-oxo-2,3,6,7,8,9,10,
11,12,13,14,15,16,17-tetradecahydro-1H-cyclopenta
[a]phenanthren-17-yl anilinoacetate 17

N-Boc-phenylglycine was prepared as described in PCT Int. App., 2007026920 and then used in accordance with general method #2. The Boc group was removed using TFA in DCM. $^1$H NMR (300 MHz, CDCl3) δ 7.19 (td, J=7.5, 2.1 Hz, 2H), 6.76 (t, J=7.5 Hz, 1H), 6.61 (dd, J=8.7, 1.2 Hz, 2H), 5.84 (s, 1H), 4.28 (bs, 1H), 3.89 (d, J=3.6 Hz, 2H), 2.65 (1H).

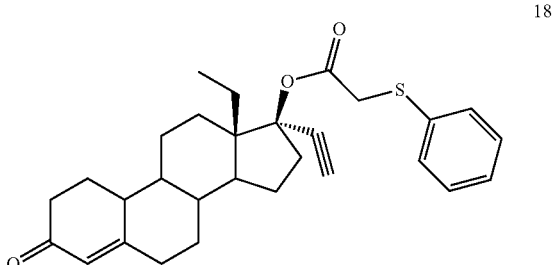

(13S,17R)-13-ethyl-17-ethynyl-3-oxo-2,3,6,7,8,9,10,
11,12,13,14,15,16,17-tetradecahydro-1H-cyclopenta
[a]phenanthren-17-yl (phenyl sulfanyl)acetate 18

Prepared in accordance with general method #2, with the exception being that anaerobic reaction conditions were carefully employed. $^1$H NMR (300 MHz, CDCl3) δ 7.45-7.40 (m, 2H), 7.34-7.20 (m, 3H), 5.84 (s, 1H), 3.61 (s, 2H), 2.60 (1H).

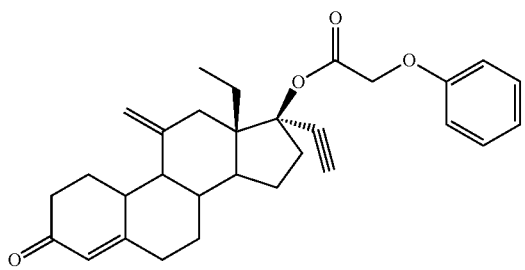

(13S,17R)-13-ethyl-17-ethynyl-11-methylidene-3-oxo-2,3,6,7,8,9,10,11,12,13,14,15,16,17-tetradeca-hydro-1H-cyclopenta[a]phenanthren-17-yl phenoxy-acetate 19

Prepared in accordance with general method #2. 1H NMR (□, CDCl3 300 MHz): 7.29 (dt, 2H, ArH, J=7.5, 0.6 Hz), 6.99 (t, 1H, ArH, J=7.5 Hz), 6.88 (d, 2H, ArH, J=7.8 Hz), 5.88 (s, 1H), 5.05 (s, 1H), 4.84 (s, 1H), 4.60 (s, 2H), 2.84 (m, 2H), 2.68 (s, 1H) 1.02 (t, 3H, CH3, J=7.2 Hz).

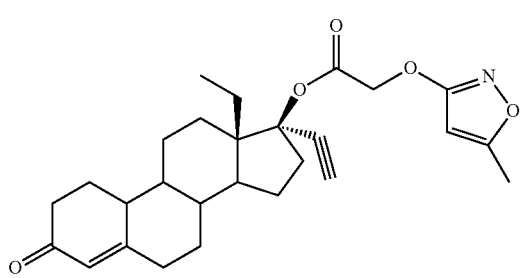

(13S,17R)-13-ethyl-17-ethynyl-3-oxo-2,3,6,7,8,9,10,11,12,13,14,15,16,17-tetradecahydro-1H-cyclopenta[a]phenanthren-17-yl [(5-methyl-1,2-oxazol-3-yl)oxy]acetate 20

Prepared in accordance with general method #1. 1H NMR (δ, CDCl3 300 MHz): 5.83 (s, 1H), 5.70 (d, 1H, J=0.6 Hz), 4.76 (s, 2H), 2.84 (m, 1H), 2.65 (s, 1H), 2.33 (t, 3H, CH3, J=0.6 Hz), 0.98 (t, 3H, CH3, J=7.3 Hz).

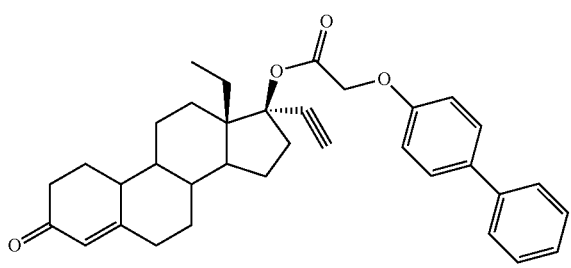

(13S,17R)-13-ethyl-17-ethynyl-3-oxo-2,3,6,7,8,9,10,11,12,13,14,15,16,17-tetradecahydro-1H-cyclopenta[a]phenanthren-17-yl [([1,1'-biphenyl]-4-yl)oxy]acetate 21

Prepared in accordance with general method #1. $^1$H NMR (300 MHz, CDCl3) δ 7.60-7.49 (m, 3H), 7.47-7.37 (m, 2H), 7.35-7.26 (m, 2H), 6.99-6.94 (m, 2H), 5.83 (s, 1H), 4.65 (s, 2H), 2.67 (s, 1H).

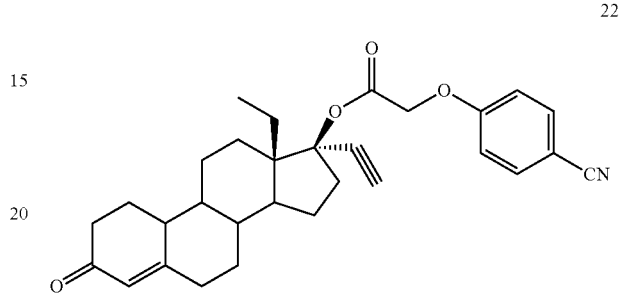

(13S,17R)-13-ethyl-17-ethynyl-3-oxo-2,3,6,7,8,9,10,11,12,13,14,15,16,17-tetradecahydro-1H-cyclopenta[a]phenanthren-17-yl (4-cyanophenoxy)acetate 22

Prepared in accordance with method #2. 1H NMR (δ, CDCl3 300 MHz): 7.99 (dd, 2H, ArH, J=2.1, 9.6 Hz), 6.93 (dd, 2H, ArH, J=2.1, 9.0 Hz), 5.82 (s, 1H), 4.65 (s, 2H), 2.79 (m, 1H), 2.66 (s, 1H) 0.95 (t, 3H, CH3, J=7.2 Hz).

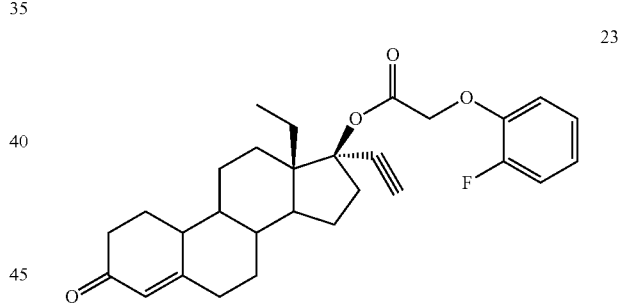

(13S,17R)-13-ethyl-17-ethynyl-3-oxo-2,3,6,7,8,9,10,11,12,13,14,15,16,17-tetradecahydro-1H-cyclopenta[a]phenanthren-17-yl (2-fluorophenoxy)acetate 23

Prepared in accordance with method #2. $^1$H NMR (δ, CDCl3 300 MHz): 6.98 (m, 4H, ArH), 5.82 (s, 1H), 4.66 (s, 2H), 2.81 (m, 1H), 2.64 (s, 1H) 0.94 (t, 3H, CH3, J=7.3 Hz).

LIST OF ABBREVIATIONS

AcCl—acetyl chloride
Boc—tertiary butyl carbamate
DCM—dichloromethane
DIC—N,N'-diisopropylcarbodiimide
DMAP—N,N-dimethyl-4-aminopyridine
DMF—N,N-dimethylformamide
DMSO—dimethyl sulfoxide
EtOAc—ethyl acetate
HPLC—high pressure liquid chromatography MHz—megahertz
NMR—nuclear magnetic resonance
TEA—triethylamine
TFA—trifluoroacetic acid
THF—tetrahydrofuran
Experimental Test Formulations:

| Formulation Vehicle | | |
|---|---|---|
| Component | Amount | Vendor |
| Benzyl alcohol | 1 g | Sigma Aldrich |
| Methyl cellulose | 1 g | Sigma Life Science |
| Sodium phosphate dibasic dehydrate | 0.752 g | Fluka Analytical |
| Sodium phosphate monobasic dihydrate | 2.99 g | Sigma Life Science |
| Water | 200 mL | Deionized |

*All solids added to water and mixed under stirring for 24 hours at ambient temperature
Mill: Fritsch pulverisette 23
Serial Number: 23.1000/00703

Original Formulation:

A stainless steel grinding bowl with a lid and seal along with three 10 mm stainless steel balls were used to formulate suspensions for injection. The compounds were weighed and added to the grinding bowl and steel balls. 1.5 mL of formulation vehicle was added to the grinding bowl, via pipette. The milling conditions used as listed: 20 minutes, 20 Hz. After milling, the suspension was transferred to a volumetric flask. Formulation vehicle was used to dilute the milled suspension to produce the desired injection dose.

Experimental Biology Testing:

Protocol: Testing Long Term Injectable Contraceptive

Adult female rats (180-200 g body weight) were used for the study (adapted over 1 week before starting the study).

For each compound, two doses were tested (2 and 4 mg/rat).

Experimental Procedure:

Long acting properties of each preparation had been determined in an estrous suppression assay using virgin, mature (180-200 g) cycling rats of Sprague-Dawley strain. Upon receipt the animals were smeared daily (procedure described as below) for cyclicity and those who were showing two consecutive cycles were used for the study. Each animal was injected subcutaneously (s.c) with 0.5 ml of the test preparation (in the vehicle as described above) on the same day regardless of the stage of the cycle. Each compound was initially tested in 6 rats. Everyday excluding weekend, smears were taken starting on the day after injection and continued until such time that cornification of vaginal epithelium was observed and cycling was re-established (Bialy G, Blye R P, Enever R P, Naqvi R H, Lindberg M C. Long-acting contraceptive agents: structure activity relationships in a series of norethisterone and levonorgestrel esters. *Steroids* 1983, v 41, p 361).

Cycle Control was Detected By Vaginal Smear as Below:

Epithelium and lamina propria of the vagina undergo characteristic changes during the cycle. This cyclical changes was used in rodents to stage cycle diagnosis (1). During the cycle, it comes to a complete replacement of the epithelium. In order to determine the stage of the cycle, vaginal solution/mucus was collected as follows. The rat was fixed with one hand. With the other hand, a small moistened cotton swab (2-3 mm diameter) was inserted into the vagina and removed by gently rotating cell material. This was done with caution, since excessive irritation could induce a pseudopregnancy stage in animals. A drop of water on a slide was applied and dabbed the cotton swab in it. The smear was assessed under the microscope (Nikon Eclipse Ti, Magnification: 10×0.25) (Nelson J F, Felicio L S, Randall P K, Sims C, Finch C E. A longitudinal study of estrous cyclicity in aging C57BL/6J mice: I. Cycle frequency, length and vaginal cytology. *Biol Reprod.* 1982 September; 27(2): 327-39).

Evaluation of Vaginal Smears in Rats:

Diestrous (Stage 1)

The smear of diestrous is characterized by some neutrophils and a few small degenerated, irregularly shaped epithelial cells.

Proestrous (Stage 2)

The microscopic image of the smear contains a moderate number of epithelial cells with large nuclei, which are usually visible as cell clusters.

Estrous (Stage 3)

The lamina propria leukocytes migrate into the epithelium. The smear is characterized by many big horny epithelial cells.

Metestrous (Stage 4)

In metestrous stage, masses of polymorphonuclear cells with some cornified epithelial cells in the smear will become visible.

TABLE 1

Classification of the cycle stages (as per Nelson et al., 1982, (2)) is depicted in the table below:

| Cycle stages | Leukocytes | Epithelial cells with nucleus | Horny epithelial cells | Mucus consistency |
|---|---|---|---|---|
| Prooestrus | −/+ Often degenerates | +/++ Regularly shaped | −/+ | Slightly viscous |
| Oestrus | — | — | ++/+++ Relatively small cells | Slightly viscous to tough |
| Metoestrus | ++/+++ | +/++ Irregularly shaped with vacuoles | +/++ | Tough |
| Dioestrus | +/+++ | + Often irregularly shaped with vacuoles | — | Thin |

TABLE 2

Anti-ovulatory activities of prodrug progestins in female rat model.

| Compound Code | Chemical Structure | Rat Anti-ovulatory Activity Days +/− 2 | |
|---|---|---|---|
| | | 2 mg | 4 mg |
| MPA | MW 386.52 | 22 | 40 |
| EC213 TMG | MW 342.47 | 19 | |
| EC600 LB | MW 382.54 | 33 | |
| EC601 | Formula Weight: 525.66 | 10 | 34 |

TABLE 2-continued
Anti-ovulatory activities of prodrug progestins in female rat model.
| Compound Code | Chemical Structure | Rat Anti-ovulatory Activity Days +/- 2 | |
|---|---|---|---|
| | | 2 mg | 4 mg |
| EC624 | 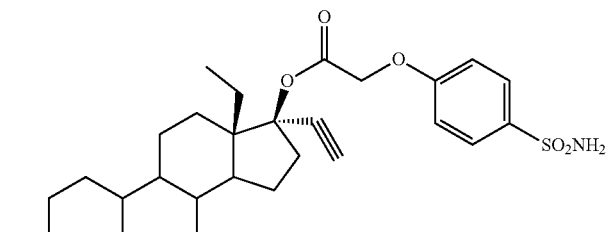 MW 525.66 | 20.5 | |
| EC625 | 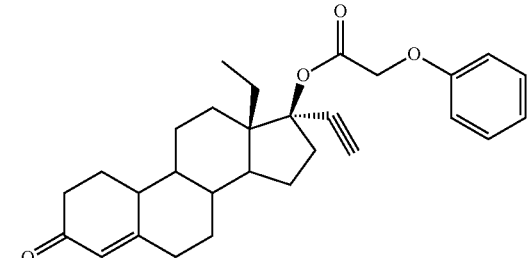 MW 446.58 | 43 | 69 |
| EC626 | 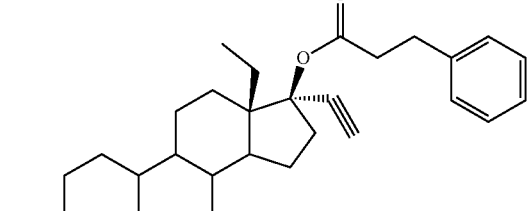 MW 444.61 | | 20 |
| EC627 | 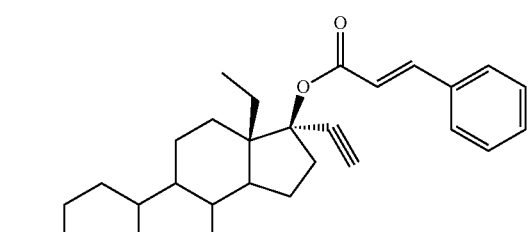 MW 442.59 | | 6 |

TABLE 2-continued
Anti-ovulatory activities of prodrug progestins in female rat model.
| Compound Code | Chemical Structure | Rat Anti-ovulatory Activity Days +/− 2 | |
|---|---|---|---|
| | | 2 mg | 4 mg |
| EC628 | 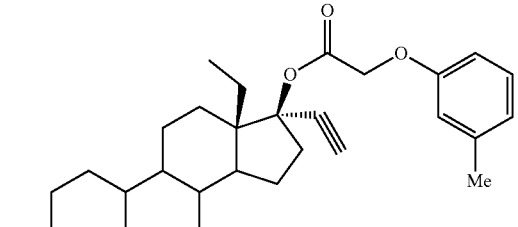 MW 460.60 | | 36 |
| EC629 | 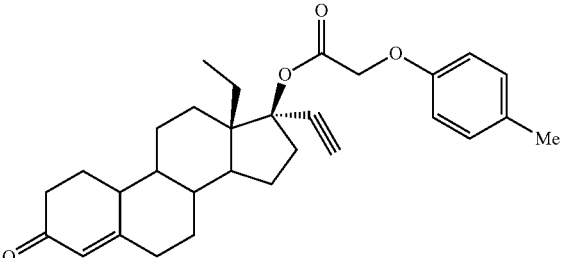 MW 460.60 | | 44.8 |
| EC630 | 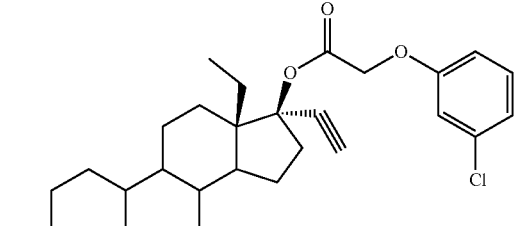 MW 481.02 | | 46.5 |
| EC631 | 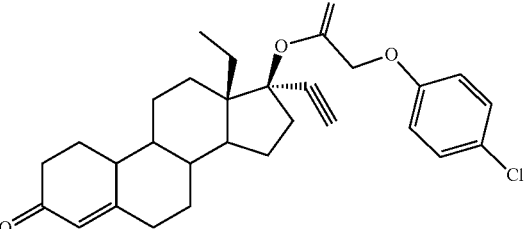 Formula Weight: 481.02 | | 33.5 |

TABLE 2-continued

Anti-ovulatory activities of prodrug progestins in female rat model.

| Compound Code | Chemical Structure | Rat Anti-ovulatory Activity Days +/− 2 | |
|---|---|---|---|
| | | 2 mg | 4 mg |
| EC632 | *(steroid structure with 2-methylphenoxyacetate ester)* Formula Weight: 460.60 | 8.5 | |
| EC633 | *(steroid structure with 2-chlorophenoxyacetate ester)* Formula Weight: 481.02 | 16.3 | |
| EC634 | *(steroid structure with 4-methoxyphenoxyacetate ester)* Formula Weight: 476.60 | 30 | |
| EC635 | *(steroid structure with 2-methoxyphenoxyacetate ester)* Formula Weight: 476.60 | 13 | |

TABLE 2-continued

Anti-ovulatory activities of prodrug progestins in female rat model.

| Compound Code | Chemical Structure | Rat Anti-ovulatory Activity Days +/− 2 | |
|---|---|---|---|
| | | 2 mg | 4 mg |
| EC636 | Formula Weight: 476.60 | 13 | |
| EC638 | MW 460.60 | 8 | |
| EC639 | MW 464.57 | 31 | |
| EC640 | MW 464.57 | 31 | |

TABLE 2-continued
Anti-ovulatory activities of prodrug progestins in female rat model.
| Compound Code | Chemical Structure | Rat Anti-ovulatory Activity Days +/− 2 | |
|---|---|---|---|
| | | 2 mg | 4 mg |
| EC641 | 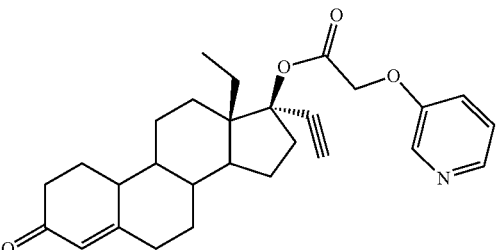 Formula Weight: 447.56 | 23 | |
| EC642 | 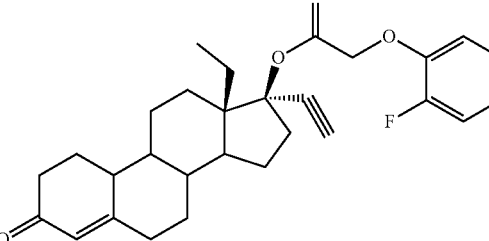 MW 464.57 | 41 | |
| EC643 | 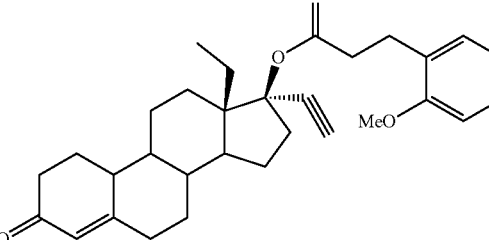 MW 474.63 | 3 | |
| EC644 | 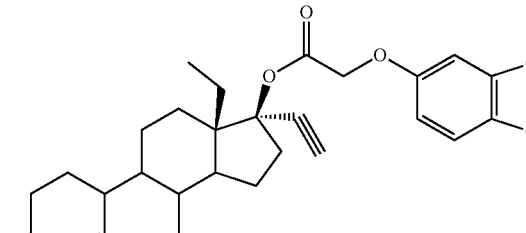 MW 490.59 | 20 | |

TABLE 2-continued
Anti-ovulatory activities of prodrug progestins in female rat model.
| Compound Code | Chemical Structure | Rat Anti-ovulatory Activity Days +/− 2 | |
|---|---|---|---|
| | | 2 mg | 4 mg |
| EC645 | 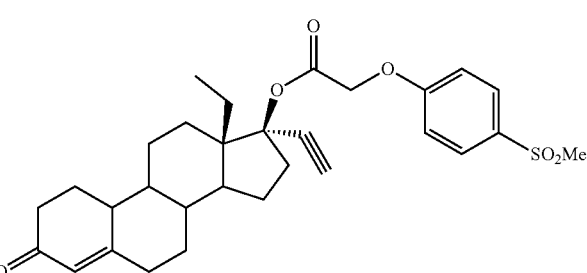<br>MW 524.67 | | 31 |
| EC646 | 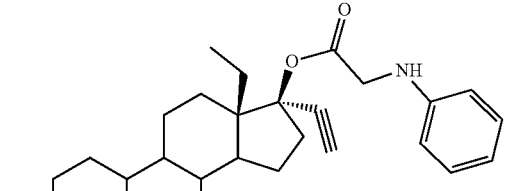<br>Formula Weight: 445.59 | | 13 |
| EC647 | 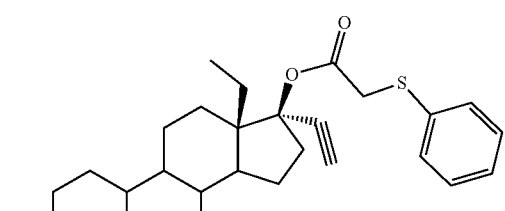<br>Formula Weight: 462.64 | | 20 |
| EC648 | 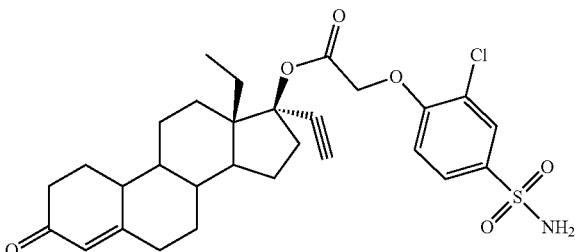<br>Formula Weight: 560.10 | | 18 |

TABLE 2-continued
Anti-ovulatory activities of prodrug progestins in female rat model.
| Compound Code | Chemical Structure | Rat Anti-ovulatory Activity Days +/− 2 | |
|---|---|---|---|
| | | 2 mg | 4 mg |
| EC649 | 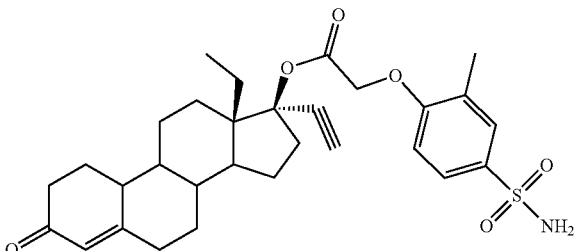 Formula Weight: 539.68 | 18.5 | |
| EC650 | 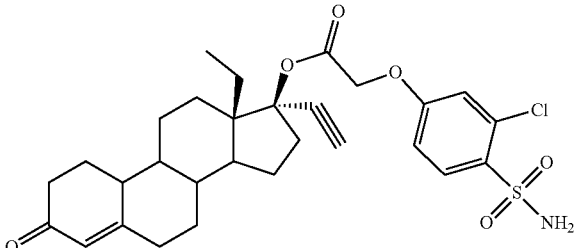 Formula Weight: 560.10 | 18.5 | |
| EC651 | EC651 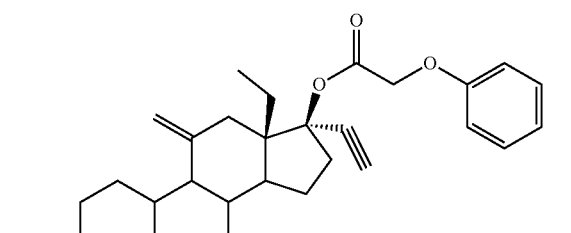 MW 458.59 | 52 | |
| EC652 | 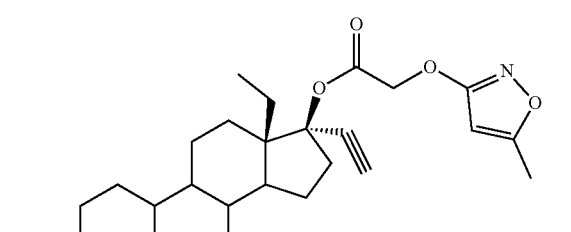 MW 451.55 | 27 | |

TABLE 2-continued
Anti-ovulatory activities of prodrug progestins in female rat model.
| Compound Code | Chemical Structure | Rat Anti-ovulatory Activity Days +/− 2 | |
|---|---|---|---|
| | | 2 mg | 4 mg |
| EC653 | 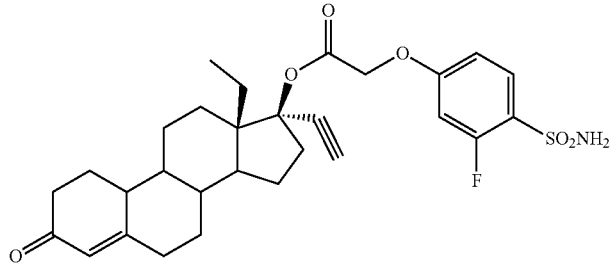<br>MW 543.65 | 15 | |
| EC654 | 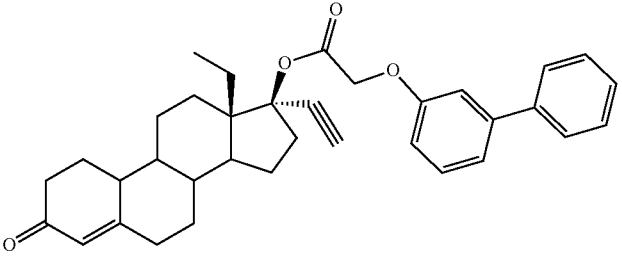<br>Formula Weight: 522.67 | 8 | |
| EC655 | 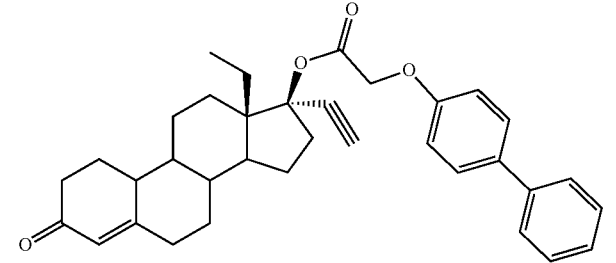<br>Formula Weight: 522.67 | 37 | |
| EC658 | 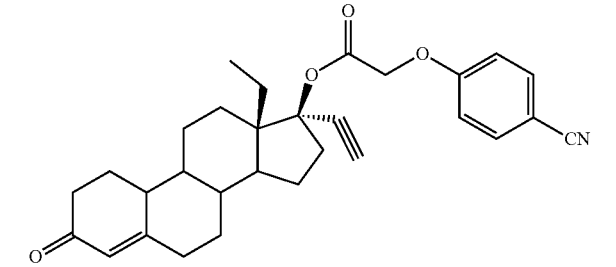<br>MW 471.59 | 29 | |

What is claimed is:

1. A compound having structural formula IIIA or IIIB:

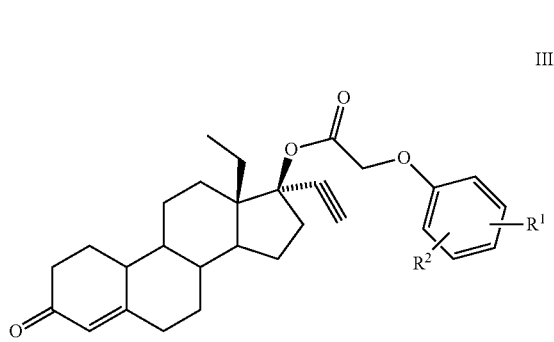

IIIA

IIIB where,

R₁, R₂ combine together to form a fused 3 to 7 membered ring with up to two heteroatoms, or each R₁, R₂, is, independently H, alkyl, cycloalkyl, phenyl, aryl, heteroaryl, acyl, cyano, halogen, OH, alkoxy, alkyl-sulfonyl or sulfonamide.

2. The compound of claim 1, wherein:

R₁, R₂ are, independently, H, alkyl, phenyl, aryl, halogen, alkoxy, alkyl-sulfonyl or sulfonamide.

3. The compound of claim 1, wherein:

R₁, R₂ are, independently, H, alkyl, phenyl, or halogen.

4. The compound of claim 1, wherein the compound has the structure:

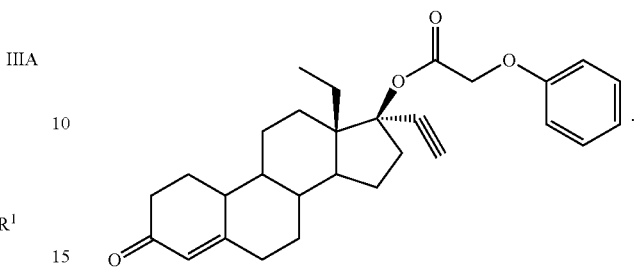

5. The compound of claim 1, wherein the compound has the structure:

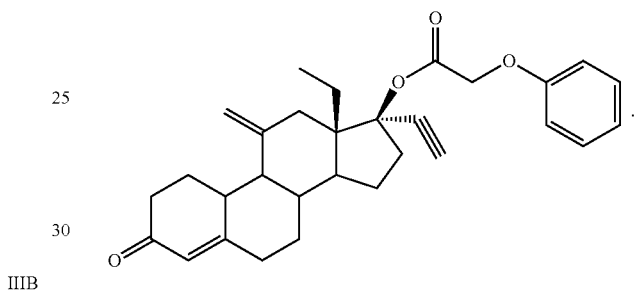

6. The compound of claim 1, wherein the compound has the structure:

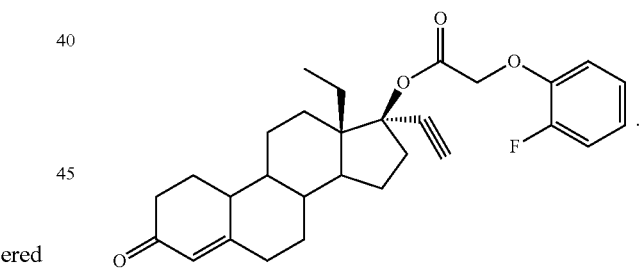

7. The compound of claim 1, wherein the compound has the structure:

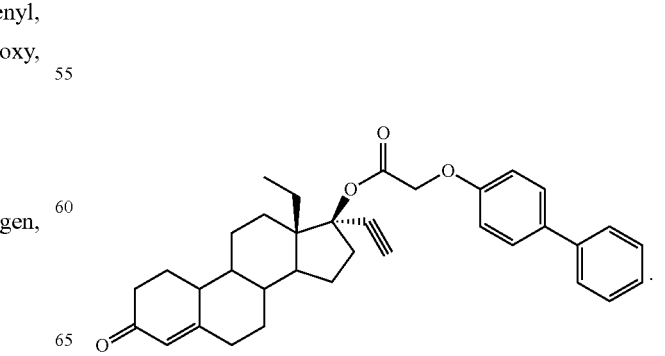

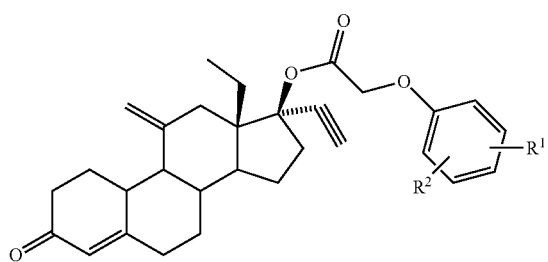

8. A compound having structural formula IVA or IVB:

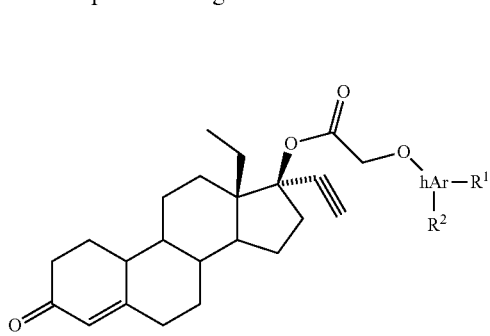

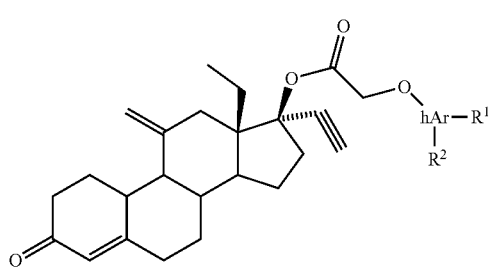

where,
hAr is pyridine, pyrimidine, pyrazine, isoxazole, or oxazole;
$R_1$, $R_2$ combine together to form a fused 3 to 7 membered ring with up to two heteroatoms, or each $R_1$, $R_2$, is, independently H, alkyl, cycloalkyl, phenyl, aryl, heteroaryl, acyl, cyano, halogen, OH, alkoxy, alkyl-sulfonyl or sulfonamide.

9. The compound of claim 8, wherein:
$R_1$, $R_2$ are, independently, H, alkyl, or phenyl.

10. The compound of claim 8, wherein the compound has the structure:

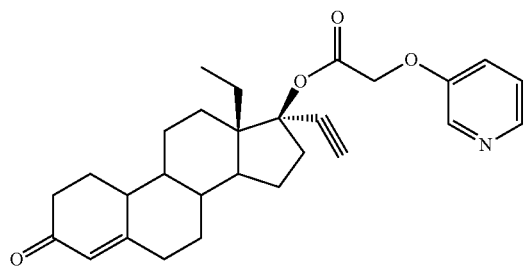

11. The compound of claim 8, wherein the compound has the structure:

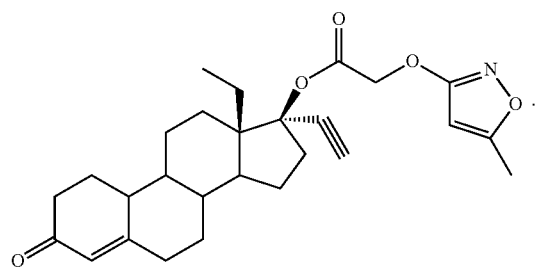 [SMILES: C#C[C@]1(OC(=O)COc2cc(C)on2)CCC2C3CCC4=CC(=O)CCC4C3CC[C@@]21CC]

12. A method of producing a contraceptive state in a subject comprising administering an effective amount of a compound, as described in claim 1, to the subject.

13. The method of claim 12, wherein the compound is administered by subcutaneous injection.

14. The method of claim 12, wherein the biological effect lasts for at least 6 months.

* * * * *